United States Patent [19]

Dreyfuss et al.

[11] Patent Number: 5,457,026

[45] Date of Patent: Oct. 10, 1995

[54] METHODS OF PROMOTING INTERMOLECULAR INTERACTIONS INVOLVING A NUCLEIC ACID

[75] Inventors: Gideon Dreyfuss, Wynnewood; Megerditch Kiledjian, Upper Darby; Douglas S. Portman, Philadelphia, all of Pa.

[73] Assignee: University of Pennsylvania, Philadelphia, Pa.

[21] Appl. No.: 980,528

[22] Filed: Nov. 20, 1992

[51] Int. Cl.[6] .................................................. C12Q 1/68
[52] U.S. Cl. ..................... 435/6; 536/23.5; 530/350
[58] Field of Search ................... 435/6; 536/23.5; 530/350

OTHER PUBLICATIONS

Freifelder, Molecular Biology, Jones and Bartlett Publishers, Inc., 1987, Boston, pp. 337 and 339.
Pontius, et al., Proc. Natl. Acad. Sci. USA (Nov. 1990) 87:8403–8407.
Kumar, et al., Biochemistry (Dec. 1990) 29(48):10717–10722.
Pontius, et al., J. Biol. Chem. (Jul. 1992) 267(20):13815–13818.
Dreyfuss, et al., Mol. Cell. Biol. 4(3) 415–423 (1984).
Dreyfuss, et al., Mol. Cell. Biol. 4(6):1104–1114 (1984).
Pinol-Roma, et al., Genes Dev. 2:215–227 (1988).
Kiledjian, et al., The EMBO Journal 11(7):2655–2664 (1992).
Pontius, et al. Proc. Natl. Acad. Sci. USA 88:8237–8241 (Sep. 1991).

*Primary Examiner*—Margaret Parr
*Assistant Examiner*—Scott W. Houtteman
*Attorney, Agent, or Firm*—Woodcock Washburn Kurtz Mackiewicz & Norris

[57] ABSTRACT

A method of promoting annealing of two nucleic acid molecules that contain complementary nucleotide sequences is disclosed. The method comprises the step of contacting the nucleic acid molecules in the presence of hnRNP U protein. A kit for hybridizing two nucleic acid molecules is disclosed. Isolated DNA molecules encoding the hnRNP U protein, expression vectors comprising the DNA molecule, host cells transformed with the expression vector and a method of producing essentially pure hnRNP U protein are disclosed. Essentially pure hnRNP U protein is disclosed. Methods of facilitating intermolecular interactions between two molecules in which at least one molecule is a nucleic acid by contacting the molecules in the presence of a protein, such as hnRNP U protein, which comprises a highly conserved "RGG box" amino acid sequence pattern are disclosed.

13 Claims, 1 Drawing Sheet

FIG. 1

METHODS OF PROMOTING INTERMOLECULAR INTERACTIONS INVOLVING A NUCLEIC ACID

FIELD OF THE INVENTION

The present invention relates to methods of promoting intermolecular interactions involving a nucleic acid molecule, to molecules useful therefor and to methods of producing such molecules. In particular, the present invention relates to a nucleic acid sequence which encodes the heterogeneous nuclear ribonucleoprotein (hnRNP) U protein, to methods of producing hnRNP U protein and to a method of promoting the annealing of nucleic acids using hnRNP U protein.

BACKGROUND OF THE INVENTION

Heterogeneous nuclear ribonucleoproteins (hnRNPs) are an abundant group of proteins which occur in the eukaryotic cell nucleus. These proteins associate with RNA polymerase II transcripts (hnRNA) to form hnRNP-complexes. The function of hnRNPs is believed to include participation in RNA processing. Originally, three groups of hnRNP proteins were isolated: the A group (A1 and A2), the B group (B1 and B2) and the C group (C1 and C2). Classically, these three groups of molecules are considered to be core proteins. At least twenty different hnRNPs have been isolated. The core protein hnRNP A1 protein is reported to facilitate RNA-RNA annealing.

Pontius, B. W. and P. Berg, *Proc. Natl. Acad. Sci. U.S.A.* (November 1990) 87:8403–8407, report that purified hnRNP A1 protein was found to promote the rapid renaturation of nucleic acid strands. It is reported that at 60° C., the A1-mediated renaturation rate was about 300-fold greater than protein-free reactions carried out at 68° C. in 1M NaCl. It is suggested that A1 may be useful in procedures that rely on nucleic acid renaturation.

Kumar, A. and S. H. Wilson, *Biochemistry* (December 1990) 29(48):10717–10722, report that hnRNP A1 is a major core protein of the mammalian hnRNP complex and that both intact hnRNP A1 protein and a C-terminal domain fragment are capable of potent strand-annealing activity for complementary base pairs of single-stranded RNA and DNA polynucleotides.

Munroe, S. H. and X. Dong, (February 1992) *Proc. Natl. Acad. Sci. USA* 89:895–899, report that the presence of hnRNP A1 protein increases the rate of annealing of complementary RNA strands by >300-fold under a wide range of salt concentrations and temperatures. The maximal annealing rates are reported to be under saturating or near saturating concentrations of protein; it is also reported that annealing decreases sharply at both higher and lower concentrations of A1. It is reported that the N-terminal two-thirds of A1 displayed very limited annealing activity while the 48 amino acid residues from the glycine-rich C-terminal region promoted annealing at a level of almost one-quarter of that which is observed with intact A1.

Pontius, B. W. and P. Berg, *J. Biol. Chem.* (July 1992) 267(20):13815–13818, report that hnRNP A1 protein affects both the equilibrium and kinetic properties of the reaction in which complementary strands of nucleic acids renature in vitro.

There are many instances where it is desirable to promote and accelerate the process of annealing complementary strands of nucleic acid sequences. For example, it is desirable to promote annealing of PCR primers in Polymerase Chain Reaction protocols. Likewise, other examples of methods in which it is desirable to promote annealing of complementary nucleic acid sequences include, but are not limited to: Southern blot hybridizations, Northern blot hybridizations, oligonucleotide and gene fragment probe hybridization of extracted RNA or DNA or colony-lift DNA, library screening hybridizations with oligonucleotides or gene fragments, subtractive hybridization, RNase protection, or primer extension assays or any technique involving primer hybridization such as DNA or RNA sequencing.

Although hnRNP protein A1 promote more efficient nucleic acid annealing, there is need for more potent and effective reagents to promote and accelerate a complementary nucleic acid sequence annealing. The applications for such reagents are numerous and the benefits of promoting and accelerating complementary nucleic acid sequence annealing provide many advantages such as, for example, enabling more rapid diagnostic testing methods as well as less time consuming laboratory procedures.

The present invention provides a method of promoting complementary nucleic acid sequence annealing using the hnRNP U protein. The hnRNP U protein is an hnRNP which promotes annealing much more efficiently than that which is accomplished using hnRNP A1. By promoting the annealing of complementary nucleic acid sequences in a method which includes providing hnRNP U protein, the annealing of complementary nucleic strands occurs a much more efficiently. In addition, the present invention provides nucleic acid sequence which encode hnRNP U protein. The nucleic acid sequence which encode hnRNP U protein may be used to produce the protein by recombinant DNA methodology. Accordingly, large quantities of essentially pure hnRNP U protein may be produced in a rapid and efficient manner.

SUMMARY OF THE INVENTION

The present invention relates to a method of promoting the annealing of two nucleic acid molecules that contain complementary nucleotide sequences. The method comprises the step of contacting two nucleic acid molecules in the presence of hnRNP U protein. The present invention relates to kits for hybridizing two nucleic acid molecules.

In addition, the present invention relates to isolated DNA molecules that encode the hnRNP U protein; expression vectors comprising the DNA molecule; host cells transformed with the expression vector; and a method of producing essentially pure hnRNP U protein. The present invention relates to essentially pure hnRNP U protein.

The present invention relates to methods of facilitating intermolecular interactions between two molecules in which at least one molecule is a nucleic acid by contacting the molecules in the presence of a protein, such as hnRNP U protein, which comprises a highly conserved "RGG box" amino acid sequence pattern.

DETAILED DESCRIPTION OF THE INVENTION

As used herein, the terms "annealing", "duplex formation" and "hybridizing" are used interchangeably and meant to refer to the non-covalent binding that occurs between complementary nucleotide substituents of polymeric nucleic acid molecules. In order for two nucleic acid molecules to anneal, it is not necessary that their respective sequences be exact matches. Depending upon hybridization condition, molecules that have varying degrees of complementarity will hybridize. Thus, the present invention relates to a method of promoting annealing of two nucleic acid molecules that contain substantially complementary nucleotide sequences which may include mismatches, deletions or additions. Such imperfectly complementary sequence will hybridize under less stringent conditions; such hybridization can also be more efficiently achieved in the presence of hnRNP U protein. As used herein, the term "complementary nucleotide sequences" is meant to refer to molecules that will hybridize under some condition due to substantial complementarity including mismatches and gaps.

The hnRNP U protein is an abundant nucleoplasmic phosphoprotein that can be crosslinked to pre-mRNA in intact cells by ultraviolet light. The hnRNP U protein was first identified as a 120 kDa protein that was co-immunopurified with antibodies that bound to other hnRNPs, indicating that it is part of a supramolecular hnRNP-complex together with other hnRNPs (Dreyfuss, G. et al. (1984) *Mol. Cell. Biol.* 4:415–423; Dreyfuss, G. et al. (1984) *Mol. Cell. Biol.* 4:1104–1114; PinolRoma, S., et al. (1988) *Genes Dev.* 2:215–227).

The presence of hnRNP U protein promotes the annealing of molecules with complementary nucleic acid sequences at an unusually high level of efficiency. This property of hnRNP U protein makes it particularly useful in a variety of applications when it is desirable to facilitate and accelerate nucleic acid annealing. The U protein or any derivative thereof can be used in a broad range of applications for promoting the annealing of nucleic acids both in vitro and in vivo. All standard techniques that involve the hybridization of nucleic acids in vitro can be improved by the addition of the hnRNP U protein. That is, the hnRNP U protein is combined with the nucleic acid molecules which are to be annealed in a reaction. The presence of the U protein in the protocol increases the efficiency by which the complementary sequences hybridize to each other.

Applications include those involving industrial processes, research protocols and diagnostic and forensic medical assays. Some examples of in vitro applications include, but are not limited to, the following protocols: Polymerase Chain Reaction (PCR), Southern blot hybridization, Northern blot hybridization, oligonucleotide and gene fragment probe hybridization of extracted RNA or DNA or colony-lift DNA, library screening hybridizations with oligonucleotides or gene fragments, subtractive hybridization, RNase protection, or primer extension assays or any technique involving primer hybridization such as DNA or RNA sequencing. The hnRNP U protein can be added as a reagent in these and other protocols and methods in which nucleic acid hybridization occurs. Essentially pure U protein can be provided in kits which can be used to promote hybridization or in kits that are used for performing the above protocols.

It is also contemplated that the U protein can be used in certain in vivo and therapeutic applications to improve the association of antisense oligonucleotides and ribozymes with their specific cellular and/or viral nucleic acid targets.

The primary structure and binding activity of hnRNP U protein is reported in Kiledjian, M. and G. Dreyfuss, *The EMBO Journal* (1992) 11(7):2655–2664, which is incorporated herein by reference. The cDNA sequence that encodes hnRNP U protein and the predicted amino acid sequence of the protein is disclosed in that reference and herein as SEQ ID NO:1.

The term "hnRNP U protein" is meant to refer to the human U protein as well as homologous U proteins from other species, and active fragments, analogs and derivatives thereof.

Using the nucleic acid sequence information disclosed in SEQ ID NO:1, one having ordinary skill in the art can clone a full-length cDNA that encodes hnRNP U protein using routine techniques without undue experimentation. Briefly, for example, the cDNA that encodes the hnRNP U protein can be identified as follows. A cDNA library can be routinely generated and screened using oligonucleotides or gene fragments that hybridize to at least a portion of SEQ ID NO:1. Likewise, PCR primers can be designed and used to produce multiple copies of SEQ ID NO:1 from cDNA prepared from extracted RNA. One having ordinary skill in the art can use the information disclosed in SEQ ID NO:1 to obtain and generate multiple copies of nucleic acid molecules that encode the hnRNP U protein by routine methods from readily available starting material.

Once DNA is isolated that encodes hnRNP U protein, it can be used by one having ordinary skill in the art to produce purified hnRNP U protein by routine methods. Briefly, for example, the DNA is first incorporated into an expression vector such as those which are commercially available. The expression vector, including the DNA that encodes hnRNP U protein, is used to transfect or transform host cells, eukaryotic or prokaryotic, that are capable of producing the protein. One having ordinary skill in the art may then isolate the protein to provide essentially pure hnRNP U protein.

While the exact concentration of U protein necessary to achieve maximum hybridization efficiency may vary as a function of hybridization conditions and nucleic acid size, concentration and type, it has been discovered that, under the conditions described below, the preferred concentration of U protein in a reaction mixture where hybridization is sought is between about 4–64 nM. The more preferred concentration of U protein in a reaction mixture where hybridization is sought is between about 10–50 nM. The most preferred concentration of U protein in a reaction mixture where hybridization is sought is between about 16–32 nM.

In some embodiments of the method of the invention, two nucleic acid molecules that comprise complementary nucleotide sequences are contacted in the presence of hnRNP U protein in order to facilitate hybridization of the two nucleic acid molecules. Either or both of the two nucleic acid molecules can be DNA or RNA or analogs thereof. DNA molecules may be genomic DNA or cDNA including genomic DNA fragments and cDNA fragments. RNA molecules may be mRNA, pre-mRNA, viralRNA or fragments thereof. At least one of the nucleic acid molecules may be an oligomer. Oligomers may be RNA or DNA and may be, for example, oligonucleotide probes or PCR primers. Gene and cDNA fragments used in hybridizations as well as genomic and RNA extracts, genomic and cDNA libraries, or digested DNA are other examples of nucleic acid molecules involved in annealing or hybridization protocols. At least one of the nucleic acid molecules may be labelled.

Generally, the protocols in which improved hybridization efficiency is desirable are standard methods performed in industrial, research and medical settings. These protocols include, as a step in each particular process, the hybridization of two nucleic acid molecules that comprise complementary nucleotide sequences. Thus, in each case, the nucleic acids are contacted in conditions that allow for hybridization. The present invention may be practiced using any of the variety of standard conditions suitable for hybridization which are used in protocols that include nucleic acid hybridization. However, some modifications may be necessary to accommodate for the U protein such as omitting components which denature or degrade the U protein. Modifications which may be necessary or desirable can be routinely identified and undertaken by those having ordinary skill in the art.

The hybridization efficiency is improved by the presence of hnRNP U protein when the two nucleic acids are contacted. The U protein promotes hybridization more efficiently than the A1 protein does.

In addition to promoting the annealing of two nucleic acid molecules that have complementary nucleic acid sequences, hnRNP U protein or related proteins may be used to effect the structure of RNA or DNA molecules such that the U protein facilitates other intermolecular interactions including those between nucleic acid molecules and other non-nucleic acid molecules such as biomolecules and biologically active molecules including proteins, carbohydrates, lipids and small molecules including drugs, salts and detergents. Thus, hnRNP U protein may be used to facilitate nucleic acid processing or modification by non-nucleic acid molecules. The nucleic acid which complexes with added hnRNP U protein is better presented or conformationally more accessible for such interaction. For example, RNA processing by ribozymes may be facilitated by hnRNP U protein.

Accordingly, in some embodiments of the present invention, interactions between a nucleic acid molecule and a non-nucleic acid molecule are facilitated and promoted when such molecules are contacted in the presence of hnRNP U protein.

In addition to the U protein and U protein equivalents, analogs and derivatives referred to herein, molecules that comprise the same active structural feature as U protein may also be used in methods to promote intermolecular interactions that include a nucleic acid molecule. Specifically, the present invention includes methods of facilitating intermolecular reactions between a nucleic acid molecule and a second molecule which include contacting the two molecules in the presence of a protein that shares structural and functional properties with the U protein. These methods include methods of promoting hybridization between two nucleic acid molecules that have complementary nucleotide sequences as well as methods of facilitating intermolecular interactions involving a nucleic acid molecule and a non-nucleic acid molecule.

The portion of the U protein which is responsible for the hybridization promoting activity that is exhibited by the molecule may reside in the carboxy terminal end of the molecule. In particular, a highly conserved amino acid sequence pattern has been identified in the U protein which is similarly present in several different proteins from different and diverse species. Each of these proteins share the common property of binding to RNA. FIG. 8 of Kiledjian, M. and G. Dreyfuss, *The EMBO Journal* (1992) 11(7):2655–2664, shows the conserved region found in diverse proteins.

The conserved amino acid sequence region is referred to herein as the "RGG box". The RGG box is a pattern of amino acid residues over a span of a polypeptide chain.

The RGG box is made up of at least 3, usually 4 or 5, amino acid triplet segments: triplets include a three residue sequence selected from the group: RGG, RRG, GRG and GGR. More often, the segments are RGG, RRG and GRG. Usually, RGG is predominantly present.

The 3–5 triplet segments occur in a span of a polypeptide between about 18 to about 26 residues in length. More often, the RGG box falls within a span of 20–24; usually within a 22–23 residue span.

Within the span that the RGG box occurs, the individual segments are divided by non-segment sequences 0–4 residues in length. Usually the interposed sequences are 0–3 residues in length; more often 0–2.

Proteins which contain the RGG box exhibit RNA binding activity and are believed to facilitate intermolecular interaction between a nucleic acid molecule and a second molecule such as a nucleic acid, protein, carbohydrate or lipid. The intermolecular interaction facilitating property, including their property of nucleic acid annealing, of hnRNP U protein is thought, at least in part, to reside in and be due to the RGG box at the carboxy end of the U protein. Other molecules which display this highly conserved sequence may also be useful to facilitate intermolecular interactions between at least one nucleic acid molecule and a second molecule such as promoting the annealing of nucleic acid molecules.

Accordingly, one aspect of the present invention relates to a method of promoting and facilitating intermolecular interactions between a nucleic acid molecule and a second molecule comprising the step of contacting the nucleic acid molecule and the second molecule in the presence of a protein that contains an RGG box. Some embodiments of the present invention relate to a method of promoting and facilitating annealing of two nucleic acid molecules that contain complementary nucleotide sequences by contacting the two nucleic acid molecules in the presence of a protein that comprises an RGG box.

In some methods of the invention, the RGG box is made up of at least 3, preferably 4 or 5, amino acid triplet segments which include triplets selected from the group: RGG, RRG, GRG and GGR. Preferably, the segments are RGG, RRG and GRG; more preferably RGG. In a particular RGG box, the triplets need not be the same. In some methods of the invention, the RGG box contains 3–5 three residue segments that occur in a span of the polypeptide between about 18 to about 26 residues in length. Preferably, the RGG box falls within a span of 20–24; more preferably within a 22–23 residue span.

According to some methods of the invention, the RGG box of the protein used contains individual segments that may be divided by non-segment sequences 0–4 residues in length. Preferably, the interposed sequences are 0–3 residues in length; more preferably 0–2. According to the invention, embodiments include the methods, described here in as using hnRNP U protein, which may also be performed using, as a substitute for U protein, a different protein which comprises an RGG box.

EXAMPLES

Example 1

The hnRNP U protein was produced in *E. coli* BL21(DE3) (Novagen, Madison Wis.) cells using the pET11 a expression system (Novagen). The cDNA which encodes the U protein was isolated as described in Kiledjian, M. and G. Dreyfuss, *The EMBO Journal* (1992) 11(7):2655–2664, and inserted into the pET11a vector. The recombinant vector was then used to transform BL21(DE3) cells by standard techniques. The transformed cells were grown in LB until $OD_{600}$ was 0.5 at which point 0.4 mM IPTG was added to induce expression of the U protein cDNA that was inserted in the expression vector. After 3 hours, the protein was harvested.

The protein was partially purified on a DEAE-Sephacel column and subsequently purified to apparent homogeneity on a single-stranded-DNA (ssDNA) cellulose column using standard procedures. U protein-expressing BL21(DE3) extract (in a 50 mM sodium phosphate buffer, pH 7.2) was bound to DEAE-Sephacel at 100 mM NaCl, washed with a 300 mM NaCl buffer and eluted with a 500 mM NaCl buffer. The eluate was diluted to a final NaCl concentration of 100 mM, bound to an ssDNA-Cellulose Column and eluted with a linear gradient of increasing NaCl to 2M salt. Fractions containing purified U protein as determined by silver-stained SDS-PAGE gel were pooled and concentrated on a Centicon 10 micro concentrator (Amicon, Beverly Mass.). Protein concentration was determined using the Bio-Rad (Richmond Calif.) protein assay dye reagent concentrate.

Example 2

The method that was employed to assay annealing promoting activity in vitro involved mixing two complementary RNA strands with the protein to be assayed under the appropriate buffer conditions as essentially described by Munroe, S. H. and X. Dong, *Proc. Natl. Acad. Sci. USA* (February 1992) 89:895–899, which is incorporated herein by reference. Briefly, an RNA transcript was combined with a relatively short (85 nucleotide), labelled RNA probe that had a sequence which was complementary to about 60 nucleotides of the RNA transcript sequence. Formation of double stranded RNA (dsRNA) was then monitored by digesting the reaction mixture with RNAse $T_1$, which degrades only the unannealed single stranded RNA (ssRNA). Resistant RNA molecules, that is double stranded molecules, were electrophoretically resolved on a denaturing polyacrylamide gel. The presence or absence of RNAse $T_1$-resistant RNA fragments provided a measure of the extent of annealing which took place before the RNase digestion. This protocol was followed using a series of different dilutions of hnRNP A1 and U protein and with control samples.

Preparation of RNA transcripts.

The two complementary RNAs employed as substrates were RSP-1-ΔIVS RNA ("sense RNA") and an internally-$^{32}$P-labeled 85 nucleotide (nt) RNA probe that contains cloned RSP-1-ΔIVS sequences.

RSP-1-ΔIVSRNA ("sense RNA") is a 454 nt pre-mRNA that was derived from the first intron and flanking exons of the adenovirus 2 tripatrite leader (Konarska, M. M. et al., *Cell* (1984) 38:731). It was transcribed in vitro from a BglI-linearized pRSP-1-ΔIVS DNA template in a standard 100 μL reaction according to the reagent manufacturer's instructions (Promega, Madison Wis.). The full length transcript was purified by denaturing electrophoresis on an 8% (30:1) acrylamide:bis/6M urea gel, visualized using 254 nm light and eluted using standard procedures. The concentration of the purified RNA was determined spectrophotometrically at 260 nm.

The internally-$^{32}$P-labeled 85 nt RNA probe was generated by in vitro transcription from pAd3'ss-60(+). Plasmid pAd3'ss-60(+) contains the sequences that span from 46 nt upstream to 14 nt downstream of the 3' splice site encoded in pRSP-1-ΔIVS which are subcloned into the EcoRI site of pGEM®-1 (Promega). The probe RNA was designed to be complementary to 60 nt of sequence surrounding the 3' splice site of the sense RNA. The probe also contained a total of 15 nt of vector-derived non-complementary sequence at the 5' and 3' ends, which existed as single-stranded overhangs that, upon annealing, were susceptible to RNAse $T_1$ digestion, generating a 60-nt protected fragment.

The $^{32}$P-labelled probe RNA was generated in a standard 50 μl reaction according to manufacturer's instructions (Promega). Isolation of the probe RNA was by the same procedure as was used in the preparation of the sense RNA described above except that the purification of probe utilized a 12% (30:1) acrylamide:bis/6M urea gel, and a full-length transcript was visualized with a 15-second exposure to Kodak X-OMAT™ AR film.

Annealing Promoting Assay.

To assay annealing promoting activity, samples of the hnRNP U protein, the hnRNP A1 protein, bovine serum albumin (BSA) or *E. coli* single strand binding protein (SSB) were each diluted to twice their desired final concentration in the assay with dilution buffer (40 mM HEPES pH 7.6, 1 mM magnesium acetate, 200 mM KCl, 0.2 mM DTT, 100 μg/μl RNase-free BSA (Pharmacia, Piscataway N.J.)) on ice in a 20 μl volume. Two-fold serial dilutions were made by sequentially mixing 10 μl of the previous dilution with an equal amount of dilution buffer yielding the final protein dilutions which were used in the experiments. An equivalent amount of undigested probe RNA was included in the experiment to verify the change in size of the probe upon RNase $T_1$ digestion. As standards for the RNase $T_1$ digestion, probe alone or pre-annealed duplex RNA (annealed with 500 mM NaCl at 65° C. for 15 minutes) were also included.

Sense and probe PuNAs were diluted in water individually to 4 nM and 2 nM, respectively, and denatured at 65° C. for 5 minutes immediately followed by chilling on ice. Final protein dilutions were then preincubated at 30° C. for 5–10 minutes. Equal volumes of the two denatured ssRNA stock solutions were then mixed together and kept on ice to minimize adventitious annealing. Annealing reactions were initiated by adding 10 μl aliquots of the ssRNA mixture to each of the protein samples at twenty second intervals. Reaction samples were kept at 30° C. during the annealing reaction. Ten minutes after the initiation of the first annealing reaction, 2.2 μl of 10 U/μl RNase $T_1$ (Calbiochem, San Diego, Calif.) were added to each reaction sample at twenty second intervals, and the reaction samples were transferred to a 37° C. bath. After fifteen minutes, 2.2 μl of 2 X stop solution (0.2% SDS, 1 mg/mL Proteinase K, 1 mg/mL *E. coli* tRNA, 600 mM sodium acetate, pH 5.2) were added to each reaction sample at twenty-second intervals. Each reaction sample was incubated at 37° C. for 15 minutes, extracted once with 25:24:1 phenol:chloroform:isoamyl alcohol, and precipitated with 2.5 volumes of ethanol overnight at −20° C.

Precipitated RNAs were pelleted by centrifugation at 4° C. for 30 minutes, washed once with 70% ethanol, air-dried, and resuspended in formamide sample buffer containing bromophenol blue and xylene cyanole FF tracking dyes. RNA fragments were resolved on 12% (30:1) acrylamide:bis/8M urea gets for 1000 Volt-hours. Gels were fixed for 45 minutes in several changes of 7% acetic acid/7% methanol, followed by 15 minutes in 10% acetic acid/50% methanol, followed by 30 minutes in several changes of 100% methanol. Gels were vacuum-dried on to Whatman 3MM filter paper for 1 hour at 80° C. and exposed for 12 hours to Amersham Hyperfilm™-MP film at −80° C. with an intensifying screen. Quantitation of the intensity of the protected band was performed directly by exposing the dried gel using the Molecular Dynamics PhosphorImager 400S and the Image Quant 3.15 software.

Results

Figure 1:
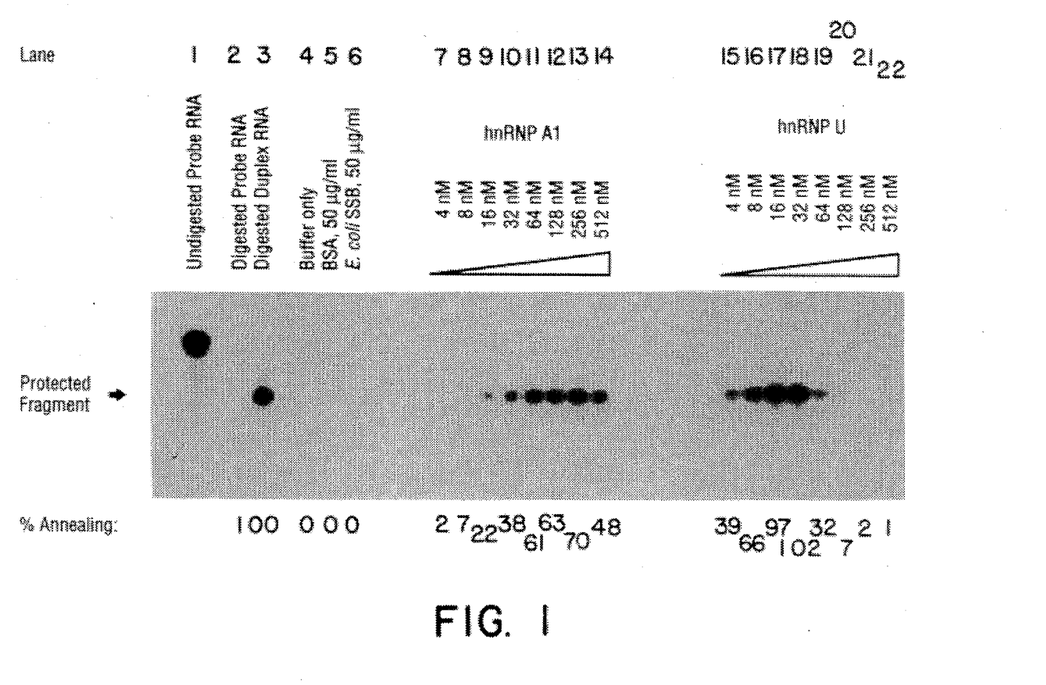
FIG. 1 is an autoradiogram of labelled RNA probes that were annealed to complementary RNA molecules in the presence of a series of dilutions of hnRNP A1 and U proteins as well as appropriate controls.

FIG. 1 shows the results of the experiment. The left most lanes are controls. Lane 1, designated undigested probe, is the $^{32}$P-labelled 85 nt RNA probe which has not been exposed to either pre-mRNA or RNase. Because it is longer than digested heteroduplex material, undigested probe travels through the gel more slowly. Lane 2, which is empty, shows that the digested single stranded probe does not show up on the assay. Lane 3 indicates the distance traveled by annealed probe that is subsequently digested. Lanes 4, 5 and 6 are annealing experiments run using Buffer only, BSA and E. coli SSB. The lack of bands indicates that no annealing occurred during the reaction time that elapsed. Lanes 7–14 are the results of annealing experiments using different concentrations of hnRNP A1 protein. Lanes 15–22 are the results of annealing experiments using different concentrations of hnRNP U protein.

The results indicate that hnRNP U protein is clearly the more effective reagent for promoting hybridization relative to protein A1. The annealing promoting activity demonstrated by hnRNP U protein is significantly more efficient than that of the A1 protein. A greater level of annealing was demonstrated using U protein as compared with A1 protein. Furthermore, lower concentrations of U protein relative to A1 protein were needed to achieve a higher level of annealing. Table 1 provides a quantitative comparison between the level of annealing promoted by the various concentrations of both hnRNP U protein and hnRNP A1 protein.

TABLE 1

| | Protein Percent (%) Annealing | |
| --- | --- | --- |
| Conc, nM | hnRNP U | hnRNP A1 |
| 4 | 38.6 | 2.0 |
| 8 | 65.9 | 7.4 |
| 16 | 97.1 | 22.1 |
| 32 | 102.2 | 38.1 |
| 64 | 31.5 | 60.6 |
| 128 | 7.4 | 62.5 |
| 256 | 2.3 | 70.3 |
| 512 | 0.6 | 47.6 |

100% value normalized to pre-annealed duplex RNA
0% value normalized to buffer only

---

We claim:

1. A method of promoting annealing of a first nucleic acid molecule to a second nucleic acid molecule wherein said first nucleic acid molecule and said second nucleic acid molecule contain nucleotide sequences that are complementary to each other;
said method comprising the step of combining in vitro said first nucleic acid molecule and said second nucleic acid molecule in the presence of human hnRNP U protein wherein said molecules anneal and wherein said hnRNP U protein has the amino acid sequence shown in SEQ ID NO:2.

2. The method of claim 1 wherein hnRNP U protein is present at a concentration of 4–64 nM.

3. The method of claim 1 wherein hnRNP U protein is present at a concentration of 10–50 nM.

4. The method of claim 1 wherein hnRNP U protein is present at a concentration of 16–32 nM.

5. The method of claim 1 wherein at least one of said first nucleic acid molecule and said second nucleic acid molecule is a DNA molecule.

6. The method of claim 1 wherein at least one of said first nucleic acid molecule and said second nucleic acid molecule is a genomic DNA molecule.

7. The method of claim 1 wherein at least one of said first nucleic acid molecule and said second nucleic acid molecule is a cDNA molecule.

8. The method of claim 1 wherein at least one of said first nucleic acid molecule and said second nucleic acid molecule is an RNA molecule.

9. The method of claim 1 wherein at least one of said first nucleic acid molecule and said second nucleic acid molecule is a mRNA molecule.

10. The method of claim 1 wherein at least one of said first nucleic acid molecule and said second nucleic acid molecule is a pre-mRNA molecule.

11. The method of claim 1 wherein at least one of said first nucleic acid molecule and said second nucleic acid molecule is viral RNA molecule.

12. The method of claim 1 wherein said annealing of said nucleic acid molecules is part of a protocol selected from the group consisting of: Polymerase Chain Reaction; Southern blot hybridization; Northern blot hybridization; an RNase protection assay; subtractive hybridization and primer extension assay.

13. The method of claim 1 wherein said annealing of said nucleic acid molecules is part of a Polymerase Chain Reaction protocol.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3223 base pairs
        ( B ) TYPE: nucleic acid
        ( C ) STRANDEDNESS: double
        ( D ) TOPOLOGY: linear     ( i i ) MOLECULE TYPE: cDNA     ( i x ) FEATURE:
        ( A ) NAME/KEY: CDS
        ( B ) LOCATION: 42..2459

( x i ) SEQUENCE DESCRIPTION: SEQ ID NO:1:

```
CGAGTTTGAG  GCAGCGCTAG  CGGTGAATCG  GGGCCCTCAC  C ATG AGT TCC TCG           53
                                                 Met Ser Ser Ser
                                                  1

CCT GTT AAT GTA AAA AAG CTG AAG GTG TCG GAG CTG AAA GAG GAG CTC           101
Pro Val Asn Val Lys Lys Leu Lys Val Ser Glu Leu Lys Glu Glu Leu
 5              10                  15                  20

AAG AAG CGA CGC CTT TCT GAC AAG GGT CTC AAG GCC GAG CTC ATG GAG          149
Lys Lys Arg Arg Leu Ser Asp Lys Gly Leu Lys Ala Glu Leu Met Glu
                 25                  30                  35

CGA CTC CAG GCT GCG CTG GAC GAC GAG GAG GCC GGG GGC CGC CCC GCC          197
Arg Leu Gln Ala Ala Leu Asp Asp Glu Glu Ala Gly Gly Arg Pro Ala
             40                  45                  50

ATG GAG CCC GGG AAC GGC AGC CTA GAC CTG GGC GGG GAT TCC GCT GGG          245
Met Glu Pro Gly Asn Gly Ser Leu Asp Leu Gly Gly Asp Ser Ala Gly
         55                  60                  65

CGC TCG GGA GCA GGC CTC GAG CAG GAG GCC GCG GCC GGC GGC GAT GAA          293
Arg Ser Gly Ala Gly Leu Glu Gln Glu Ala Ala Ala Gly Gly Asp Glu
     70                  75                  80
```

| | | | | | | | | | | | | | | | | |
|---|---|---|---|---|---|---|---|---|---|---|---|---|---|---|---|---|
| GAG | GAG | GAA | GAA | GAG | GAA | GAG | GAG | GAG | GAA | GGA | ATC | TCC | GCT | CTG | GAC | 341 |
| Glu | Glu | Glu | Glu | Glu | Glu | Glu | Glu | Glu | Glu | Gly | Ile | Ser | Ala | Leu | Asp | |
| 85 | | | | 90 | | | | 95 | | | | | | | 100 | |
| GGC | GAC | CAG | ATG | GAG | CTA | GGA | GAG | GAG | AAC | GGG | GCC | GCG | GGG | GCG | GCC | 389 |
| Gly | Asp | Gln | Met | Glu | Leu | Gly | Glu | Glu | Asn | Gly | Ala | Ala | Gly | Ala | Ala | |
| | | | 105 | | | | | 110 | | | | | 115 | | | |
| GAC | TCG | GGC | CCG | ATG | GAG | GAG | GAG | GAG | GCC | GCC | TCG | GAA | GAC | GAG | AAC | 437 |
| Asp | Ser | Gly | Pro | Met | Glu | Glu | Glu | Glu | Ala | Ala | Ser | Glu | Asp | Glu | Asn | |
| | | | 120 | | | | | 125 | | | | | 130 | | | |
| GGC | GAC | GAT | CAG | GGT | TTC | CAG | GAA | GGG | GAA | GAT | GAG | CTC | GGG | GAC | GAA | 485 |
| Gly | Asp | Asp | Gln | Gly | Phe | Gln | Glu | Gly | Glu | Asp | Glu | Leu | Gly | Asp | Glu | |
| | | | 135 | | | | | 140 | | | | | 145 | | | |
| GAG | GAA | GGC | GCG | GGC | GAC | GAG | AAC | GGG | CAC | GGG | GAG | CAG | CAG | CCT | CAA | 533 |
| Glu | Glu | Gly | Ala | Gly | Asp | Glu | Asn | Gly | His | Gly | Glu | Gln | Gln | Pro | Gln | |
| 150 | | | | | 155 | | | | | 160 | | | | | | |
| CCG | CCG | GCG | ACG | CAG | CAG | CAA | CAG | CCC | CAA | CAG | CAG | CGC | GGG | GCC | GCC | 581 |
| Pro | Pro | Ala | Thr | Gln | Gln | Gln | Gln | Pro | Gln | Gln | Gln | Arg | Gly | Ala | Ala | |
| 165 | | | | | 170 | | | | | 175 | | | | | 180 | |
| AAG | GAG | GCC | GCG | GGG | AAG | AGC | AGC | GGC | CCC | ACC | TCG | CTG | TTC | GCG | GTG | 629 |
| Lys | Glu | Ala | Ala | Gly | Lys | Ser | Ser | Gly | Pro | Thr | Ser | Leu | Phe | Ala | Val | |
| | | | | 185 | | | | | 190 | | | | | 195 | | |
| ACG | GTG | GCG | CCG | CCC | GGG | GCG | AGG | CAG | GGC | CAG | CAG | CAG | GCG | GGA | GGG | 677 |
| Thr | Val | Ala | Pro | Pro | Gly | Ala | Arg | Gln | Gly | Gln | Gln | Gln | Ala | Gly | Gly | |
| | | | 200 | | | | | 205 | | | | | 210 | | | |
| GAC | GGC | AAA | ACA | GAA | CAG | AAA | GGC | GGA | GAT | AAG | AAG | AGG | GGT | GTT | AAA | 725 |
| Asp | Gly | Lys | Thr | Glu | Gln | Lys | Gly | Gly | Asp | Lys | Lys | Arg | Gly | Val | Lys | |
| | | | 215 | | | | | 220 | | | | | 225 | | | |
| AGA | CCA | CGA | GAA | GAT | CAT | GGC | CGT | GGA | TAT | TTT | GAG | TAC | ATT | GAA | GAG | 773 |
| Arg | Pro | Arg | Glu | Asp | His | Gly | Arg | Gly | Tyr | Phe | Glu | Tyr | Ile | Glu | Glu | |
| | | 230 | | | | | 235 | | | | | 240 | | | | |
| AAC | AAG | TAT | AGC | AGA | GCC | AAA | TCT | CCT | CAG | CCA | CCT | GTT | GAA | GAA | GAA | 821 |
| Asn | Lys | Tyr | Ser | Arg | Ala | Lys | Ser | Pro | Gln | Pro | Pro | Val | Glu | Glu | Glu | |
| 245 | | | | | 250 | | | | | 255 | | | | | 260 | |
| GAT | GAA | CAC | TTC | GAT | GAC | ACA | GTG | GTT | TGT | CTT | GAT | ACT | TAT | AAT | TGT | 869 |
| Asp | Glu | His | Phe | Asp | Asp | Thr | Val | Val | Cys | Leu | Asp | Thr | Tyr | Asn | Cys | |
| | | | | 265 | | | | | 270 | | | | | 275 | | |
| GAT | CTA | CAT | TTT | AAA | ATA | TCA | AGA | GAT | CGT | CTC | AGT | GCT | TCT | TCC | CTT | 917 |
| Asp | Leu | His | Phe | Lys | Ile | Ser | Arg | Asp | Arg | Leu | Ser | Ala | Ser | Ser | Leu | |
| | | | 280 | | | | | 285 | | | | | 290 | | | |
| ACA | ATG | GAG | AGT | TTT | GCT | TTT | CTT | TGG | GCT | GGA | GGA | AGA | GCA | TCC | TAT | 965 |
| Thr | Met | Glu | Ser | Phe | Ala | Phe | Leu | Trp | Ala | Gly | Gly | Arg | Ala | Ser | Tyr | |
| | | 295 | | | | | 300 | | | | | 305 | | | | |
| GGT | GTG | TCA | AAA | GGC | AAA | GTG | TGT | TTT | GAG | ATG | AAG | GTT | ACA | GAG | AAG | 1013 |
| Gly | Val | Ser | Lys | Gly | Lys | Val | Cys | Phe | Glu | Met | Lys | Val | Thr | Glu | Lys | |
| | | 310 | | | | | 315 | | | | | 320 | | | | |
| ATC | CCA | GTA | AGG | CAT | TTA | TAT | ACA | AAA | GAT | ATT | GAC | ATA | CAT | GAA | GTT | 1061 |
| Ile | Pro | Val | Arg | His | Leu | Tyr | Thr | Lys | Asp | Ile | Asp | Ile | His | Glu | Val | |
| 325 | | | | | 330 | | | | | 335 | | | | | 340 | |
| CGT | ATT | GGC | TGG | TCA | CTA | ACT | ACA | AGT | GGA | ATG | TTA | CTT | GGT | GAA | GAA | 1109 |
| Arg | Ile | Gly | Trp | Ser | Leu | Thr | Thr | Ser | Gly | Met | Leu | Leu | Gly | Glu | Glu | |
| | | | | 345 | | | | | 350 | | | | | 355 | | |
| GAA | TTT | TCT | TAT | GGG | TAT | TCT | CTA | AAA | GGA | ATA | AAA | ACA | TGC | AAC | TGT | 1157 |
| Glu | Phe | Ser | Tyr | Gly | Tyr | Ser | Leu | Lys | Gly | Ile | Lys | Thr | Cys | Asn | Cys | |
| | | | 360 | | | | | 365 | | | | | 370 | | | |
| GAG | ACT | GAA | GAT | TAT | GGA | GAA | AAG | TTT | GAT | GAA | AAT | GAT | GTG | ATT | ACA | 1205 |
| Glu | Thr | Glu | Asp | Tyr | Gly | Glu | Lys | Phe | Asp | Glu | Asn | Asp | Val | Ile | Thr | |
| | | 375 | | | | | 380 | | | | | 385 | | | | |
| TGT | TTT | GCT | AAC | TTT | GAA | AGT | GAT | GAA | GTA | GAA | CTC | TCG | TAT | GCT | AAG | 1253 |
| Cys | Phe | Ala | Asn | Phe | Glu | Ser | Asp | Glu | Val | Glu | Leu | Ser | Tyr | Ala | Lys | |
| | | 390 | | | | | 395 | | | | | 400 | | | | |

```
AAT GGA CAA GAT CTT GGC GTT GCC TTC AAA ATC AGT AAG GAA GTT CTT         1301
Asn Gly Gln Asp Leu Gly Val Ala Phe Lys Ile Ser Lys Glu Val Leu
405             410             415                 420

GCT GGA CGG CCA CTG TTC CCG CAT GTT CTC TGC CAC AAC TGT GCA GTT         1349
Ala Gly Arg Pro Leu Phe Pro His Val Leu Cys His Asn Cys Ala Val
                425             430             435

GAA TTT AAT TTT GGT CAG AAG GAA AAG CCA TAT TTT CCA ATA CCT GAA         1397
Glu Phe Asn Phe Gly Gln Lys Glu Lys Pro Tyr Phe Pro Ile Pro Glu
            440             445             450

GAG TAT ACT TTC ATC CAG AAC GTC CCC TTA GAG GAT CGA GTT AGA GGA         1445
Glu Tyr Thr Phe Ile Gln Asn Val Pro Leu Glu Asp Arg Val Arg Gly
        455             460             465

CCA AAG GGG CCT GAA GAG AAG AAA GAT TGT GAA GTT GTG ATG ATG ATT         1493
Pro Lys Gly Pro Glu Glu Lys Lys Asp Cys Glu Val Val Met Met Ile
470             475             480

GGC TTG CCA GGA GCT GGA AAA ACT ACC TGG GTT ACT AAA CAT GCA GCA         1541
Gly Leu Pro Gly Ala Gly Lys Thr Thr Trp Val Thr Lys His Ala Ala
485             490             495             500

GAA AAT CCA GGG AAA TAT AAC ATT CTT GGC ACA AAT ACT ATT ATG GAT         1589
Glu Asn Pro Gly Lys Tyr Asn Ile Leu Gly Thr Asn Thr Ile Met Asp
            505             510             515

AAG ATG ATG GTG GCA GGT TTT AAG AAG CAA ATG GCA GAT ACT GGA AAA         1637
Lys Met Met Val Ala Gly Phe Lys Lys Gln Met Ala Asp Thr Gly Lys
        520             525             530

CTG AAC ACA CTG TTG CAG AGA GCC CCC CAG TGT CTT GGG AAA TTT ATT         1685
Leu Asn Thr Leu Leu Gln Arg Ala Pro Gln Cys Leu Gly Lys Phe Ile
535             540             545

GAG ATT GCT GCC CGA AAG AAG CGA AAT TTT ATT CTG GAT CAG ACA AAT         1733
Glu Ile Ala Ala Arg Lys Lys Arg Asn Phe Ile Leu Asp Gln Thr Asn
550             555             560

GTG TCT GCT GCT GCC CAG AGG AGA AAA ATG TGC CTG TTT GCA GGC TTC         1781
Val Ser Ala Ala Ala Gln Arg Arg Lys Met Cys Leu Phe Ala Gly Phe
565             570             575             580

CAG CGA AAA GCT GTT GTA GTT TGC CCA AAA GAT GAA GAC TAT AAG CAA         1829
Gln Arg Lys Ala Val Val Val Cys Pro Lys Asp Glu Asp Tyr Lys Gln
            585             590             595

AGA ACA CAG AAG AAA GCA GAA GTA GAG GGG AAA GAC CTA CCA GAA CAT         1877
Arg Thr Gln Lys Lys Ala Glu Val Glu Gly Lys Asp Leu Pro Glu His
        600             605             610

GCG GTC CTC AAA ATG AAA GGA AAC TTT ACC CTC CCA GAG GTA GCT GAG         1925
Ala Val Leu Lys Met Lys Gly Asn Phe Thr Leu Pro Glu Val Ala Glu
615             620             625

TGC TTT GAT GAA ATA ACC TAT GTT GAA CTT CAG AAG GAA GAA GCC CAA         1973
Cys Phe Asp Glu Ile Thr Tyr Val Glu Leu Gln Lys Glu Glu Ala Gln
630             635             640

AAA CTC TTG GAG CAA TAT AAG GAA GAA AGC AAA AAG GCT CTT CCA CCA         2021
Lys Leu Leu Glu Gln Tyr Lys Glu Glu Ser Lys Lys Ala Leu Pro Pro
645             650             655             660

GAA AAG AAA CAG AAC ACT GGC TCA AAG AAA AGC AAT AAA AAT AAG AGT         2069
Glu Lys Lys Gln Asn Thr Gly Ser Lys Lys Ser Asn Lys Asn Lys Ser
            665             670             675

GGC AAG AAC CAG TTT AAC AGA GGT GGT GGC CAT AGA GGA CGT GGA GGA         2117
Gly Lys Asn Gln Phe Asn Arg Gly Gly Gly His Arg Gly Arg Gly Gly
        680             685             690

CTC AAT ATG CGT GGT GGA AAT TTC AGA GGA GGA GCC CCT GGG AAT CGT         2165
Leu Asn Met Arg Gly Gly Asn Phe Arg Gly Gly Ala Pro Gly Asn Arg
695             700             705

GGC GGA TAT AAT AGG AGG GGC AAC ATG CCA CAG AGA GGT GGT GGC GGT         2213
Gly Gly Tyr Asn Arg Arg Gly Asn Met Pro Gln Arg Gly Gly Gly Gly
```

-continued

```
         710                          715                          720
GGA GGA AGT GGT GGA ATC GGC TAT CCA TAC CCT CGT GCC CCT GTT TTT              2261
Gly Gly Ser Gly Gly Ile Gly Tyr Pro Tyr Pro Arg Ala Pro Val Phe
725             730                 735                     740

CCT GGC CGT GGT AGT TAC TCA AAC AGA GGG AAC TAC AAC AGA GGT GGA              2309
Pro Gly Arg Gly Ser Tyr Ser Asn Arg Gly Asn Tyr Asn Arg Gly Gly
                745                 750                     755

ATG CCC AAC AGA GGG AAC TAC AAC CAG AAC TTC AGA GGA CGA GGA AAC              2357
Met Pro Asn Arg Gly Asn Tyr Asn Gln Asn Phe Arg Gly Arg Gly Asn
            760                 765                     770

AAT CGT GGC TAC AAA AAT CAA TCT CAG GGC TAC AAC CAG TGG CAG CAG              2405
Asn Arg Gly Tyr Lys Asn Gln Ser Gln Gly Tyr Asn Gln Trp Gln Gln
        775                 780                     785

GGT CAA TTC TGG GGT CAG AAG CCA TGG AGT CAG CAT TAT CAC CAA GGA              2453
Gly Gln Phe Trp Gly Gln Lys Pro Trp Ser Gln His Tyr His Gln Gly
    790                 795                     800

TAT TAT TGAATACCCA AATAAAACGA ACTGATACAT ATTTCTCCAA AACCTTCACA               2509
Tyr Tyr
805

AGAAGTCGAC TGTTTTCTTT AGTAGGCTAA CTTTTTAAAC ATTCCACAAG AGGAAGTGCC            2569

TGCGGGTTCC TTTTTTAGAA GCTTTGTGGG TTGATTTTTT TTCTTTTCTT TTTTGTACAT            2629

TTTTAATTGC AGTTTAAAAG TGAATCGTAA GAGAACCTCA GCATTGTGCA CGATAAGAGA            2689

ATGTGTCAGT ATTTCAGGGT TCTACATTTA TCTGTAAAAT GTGACTTTTT TTTTTTTTTA            2749

TCACAACAGA AGTAAAATGT TGCTTTGTAC CTGGTGTCTT TTATTAAGAA TTTACTCCCC            2809

CCATTTCTCA CAGAGAATAA CAGTCGGGAG TCATTGTCAC AATATAATAG AAATGTTAGC            2869

AACCAGATTC ATGTAAGGAC TAAGTGGTCC TCATGAATTG CATTAAGACT CTGTACTGCT            2929

CATATTACAC TCCATCCTCT CTGTAGTTTG CTGGGTAGTG GAGGGGGTAA GCTAAATCAT            2989

AGTTTCTGAC AATAACTGGG AAGGTTTTTT CTTAAAATAA CAATGGAATT GGTATAATTG            3049

GGATTGAAAA CTAAAACTTG GAACTAAGAT AGAGAAGATG GAGTGTATGT AGAAGGGCTG            3109

TTAAAAATGT AAAACTTGGT TGCATTATTT GTGGAGGCTC AAACTTGTGA AGGTTAATAC            3169

CATAATTTTT CCATTTGTTC TGCATTTGA TTCTGAAAAG AAAGCTGGCT TTGC                   3223
```

( 2 ) INFORMATION FOR SEQ ID NO:2:

( i ) SEQUENCE CHARACTERISTICS:
        ( A ) LENGTH: 806 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

```
Met Ser Ser Ser Pro Val Asn Val Lys Lys Leu Lys Val Ser Glu Leu
 1               5                  10                      15

Lys Glu Glu Leu Lys Lys Arg Arg Leu Ser Asp Lys Gly Leu Lys Ala
            20                  25                  30

Glu Leu Met Glu Arg Leu Gln Ala Ala Leu Asp Asp Glu Ala Gly
            35                  40                  45

Gly Arg Pro Ala Met Glu Pro Gly Asn Gly Ser Leu Asp Leu Gly Gly
    50                  55                      60

Asp Ser Ala Gly Arg Ser Gly Ala Gly Leu Glu Gln Glu Ala Ala Ala
65                  70                  75                  80

Gly Gly Asp Glu Glu Glu Glu Glu Glu Glu Glu Glu Glu Glu Gly Ile
                85                  90                      95
```

-continued

| | | | | | | | | | | | | | |
|---|---|---|---|---|---|---|---|---|---|---|---|---|---|
|Ser|Ala|Leu|Asp<br>100|Gly|Asp|Gln|Met|Glu<br>105|Leu|Gly|Glu|Glu|Asn<br>110|Gly|Ala|
|Ala|Gly|Ala<br>115|Ala|Asp|Ser|Gly|Pro<br>120|Met|Glu|Glu|Glu<br>125|Glu|Ala|Ala|Ser|
|Glu|Asp<br>130|Glu|Asn|Gly|Asp|Asp<br>135|Gln|Gly|Phe|Gln|Glu<br>140|Gly|Glu|Asp|Glu|
|Leu<br>145|Gly|Asp|Glu|Glu|Glu<br>150|Gly|Ala|Gly|Asp|Glu<br>155|Asn|Gly|His|Gly|Glu<br>160|
|Gln|Gln|Pro|Gln|Pro<br>165|Pro|Ala|Thr|Gln|Gln<br>170|Gln|Gln|Pro|Gln|Gln<br>175|Gln|
|Arg|Gly|Ala|Ala<br>180|Lys|Glu|Ala|Ala|Gly<br>185|Lys|Ser|Ser|Gly|Pro<br>190|Thr|Ser|
|Leu|Phe|Ala<br>195|Val|Thr|Val|Ala|Pro<br>200|Pro|Gly|Ala|Arg|Gln<br>205|Gly|Gln|Gln|
|Gln|Ala<br>210|Gly|Gly|Asp|Gly|Lys<br>215|Thr|Glu|Gln|Lys|Gly<br>220|Gly|Asp|Lys|Lys|
|Arg<br>225|Gly|Val|Lys|Arg|Pro<br>230|Arg|Glu|Asp|His|Gly<br>235|Arg|Gly|Tyr|Phe|Glu<br>240|
|Tyr|Ile|Glu|Glu|Asn<br>245|Lys|Tyr|Ser|Arg|Ala<br>250|Lys|Ser|Pro|Gln|Pro<br>255|Pro|
|Val|Glu|Glu|Glu<br>260|Asp|Glu|His|Phe|Asp<br>265|Asp|Thr|Val|Val|Cys<br>270|Leu|Asp|
|Thr|Tyr|Asn<br>275|Cys|Asp|Leu|His|Phe<br>280|Lys|Ile|Ser|Arg|Asp<br>285|Arg|Leu|Ser|
|Ala|Ser<br>290|Ser|Leu|Thr|Met|Glu<br>295|Ser|Phe|Ala|Phe|Leu<br>300|Trp|Ala|Gly|Gly|
|Arg<br>305|Ala|Ser|Tyr|Gly|Val<br>310|Ser|Lys|Gly|Lys|Val<br>315|Cys|Phe|Glu|Met|Lys<br>320|
|Val|Thr|Glu|Lys|Ile<br>325|Pro|Val|Arg|His|Leu<br>330|Tyr|Thr|Lys|Asp|Ile<br>335|Asp|
|Ile|His|Glu|Val<br>340|Arg|Ile|Gly|Trp|Ser<br>345|Leu|Thr|Thr|Ser|Gly<br>350|Met|Leu|
|Leu|Gly|Glu|Glu<br>355|Glu|Phe|Ser|Tyr|Gly<br>360|Tyr|Ser|Leu|Lys|Gly<br>365|Ile|Lys|
|Thr|Cys<br>370|Asn|Cys|Glu|Thr|Glu<br>375|Asp|Tyr|Gly|Glu|Lys<br>380|Phe|Asp|Glu|Asn|
|Asp<br>385|Val|Ile|Thr|Cys|Phe<br>390|Ala|Asn|Phe|Glu|Ser<br>395|Asp|Glu|Val|Glu|Leu<br>400|
|Ser|Tyr|Ala|Lys|Asn<br>405|Gly|Gln|Asp|Leu|Gly<br>410|Val|Ala|Phe|Lys|Ile<br>415|Ser|
|Lys|Glu|Val|Leu<br>420|Ala|Gly|Arg|Pro|Leu<br>425|Phe|Pro|His|Val|Leu<br>430|Cys|His|
|Asn|Cys|Ala<br>435|Val|Glu|Phe|Asn|Phe<br>440|Gly|Gln|Lys|Glu|Lys<br>445|Pro|Tyr|Phe|
|Pro|Ile<br>450|Pro|Glu|Glu|Tyr|Thr<br>455|Phe|Ile|Gln|Asn|Val<br>460|Pro|Leu|Glu|Asp|
|Arg<br>465|Val|Arg|Gly|Pro|Lys<br>470|Gly|Pro|Glu|Glu|Lys<br>475|Lys|Asp|Cys|Glu|Val<br>480|
|Val|Met|Met|Ile|Gly<br>485|Leu|Pro|Gly|Ala|Gly<br>490|Lys|Thr|Thr|Trp|Val<br>495|Thr|
|Lys|His|Ala|Ala<br>500|Glu|Asn|Pro|Gly|Lys<br>505|Tyr|Asn|Ile|Leu|Gly<br>510|Thr|Asn|

-continued

| | | | | | | | | | | | | | | | |
|---|---|---|---|---|---|---|---|---|---|---|---|---|---|---|---|
| Thr | Ile | Met 515 | Asp | Lys | Met | Met | Val 520 | Ala | Gly | Phe | Lys | Lys 525 | Gln | Met | Ala |
| Asp | Thr 530 | Gly | Lys | Leu | Asn | Thr 535 | Leu | Leu | Gln | Arg | Ala 540 | Pro | Gln | Cys | Leu |
| Gly 545 | Lys | Phe | Ile | Glu | Ile 550 | Ala | Ala | Arg | Lys | Lys 555 | Arg | Asn | Phe | Ile | Leu 560 |
| Asp | Gln | Thr | Asn | Val 565 | Ser | Ala | Ala | Ala | Gln 570 | Arg | Arg | Lys | Met | Cys 575 | Leu |
| Phe | Ala | Gly | Phe 580 | Gln | Arg | Lys | Ala | Val 585 | Val | Val | Cys | Pro | Lys 590 | Asp | Glu |
| Asp | Tyr | Lys 595 | Gln | Arg | Thr | Gln | Lys 600 | Lys | Ala | Glu | Val | Glu 605 | Gly | Lys | Asp |
| Leu | Pro 610 | Glu | His | Ala | Val | Leu 615 | Lys | Met | Lys | Gly | Asn 620 | Phe | Thr | Leu | Pro |
| Glu 625 | Val | Ala | Glu | Cys | Phe 630 | Asp | Glu | Ile | Thr | Tyr 635 | Val | Glu | Leu | Gln | Lys 640 |
| Glu | Glu | Ala | Gln | Lys 645 | Leu | Leu | Glu | Gln | Tyr 650 | Lys | Glu | Glu | Ser | Lys 655 | Lys |
| Ala | Leu | Pro | Pro 660 | Glu | Lys | Lys | Gln | Asn 665 | Thr | Gly | Ser | Lys | Lys 670 | Ser | Asn |
| Lys | Asn | Lys 675 | Ser | Gly | Lys | Asn | Gln 680 | Phe | Asn | Arg | Gly | Gly 685 | Gly | His | Arg |
| Gly | Arg 690 | Gly | Gly | Leu | Asn | Met 695 | Arg | Gly | Gly | Asn | Phe 700 | Arg | Gly | Gly | Ala |
| Pro 705 | Gly | Asn | Arg | Gly | Gly 710 | Tyr | Asn | Arg | Arg | Gly 715 | Asn | Met | Pro | Gln | Arg 720 |
| Gly | Gly | Gly | Gly | Gly 725 | Gly | Ser | Gly | Gly | Ile 730 | Gly | Tyr | Pro | Tyr | Pro 735 | Arg |
| Ala | Pro | Val | Phe 740 | Pro | Gly | Arg | Gly | Ser 745 | Tyr | Ser | Asn | Arg | Gly 750 | Asn | Tyr |
| Asn | Arg | Gly 755 | Gly | Met | Pro | Asn | Arg 760 | Gly | Asn | Tyr | Asn | Gln 765 | Asn | Phe | Arg |
| Gly | Arg 770 | Gly | Asn | Asn | Arg | Gly 775 | Tyr | Lys | Asn | Gln | Ser 780 | Gln | Gly | Tyr | Asn |
| Gln 785 | Trp | Gln | Gln | Gly | Gln 790 | Phe | Trp | Gly | Gln | Lys 795 | Pro | Trp | Ser | Gln | His 800 |
| Tyr | His | Gln | Gly | Tyr 805 | Tyr | | | | | | | | | | |